United States Patent
Degen et al.

(10) Patent No.: US 11,553,880 B2
(45) Date of Patent: Jan. 17, 2023

(54) IMPLANT WITH SENSOR ASSEMBLY

(71) Applicant: BIOTRONIK AG, Buelach (CH)

(72) Inventors: Nicolas Degen, Beringen (CH); Thomas Finnberg, Barsbuettel (DE)

(73) Assignee: BIOTRONIK AG, Buelach (CH)

( * ) Notice: Subject to any disclaimer, the term of this patent is extended or adjusted under 35 U.S.C. 154(b) by 162 days.

(21) Appl. No.: 16/803,359

(22) Filed: Feb. 27, 2020

(65) Prior Publication Data
US 2020/0196953 A1 Jun. 25, 2020

Related U.S. Application Data

(63) Continuation of application No. PCT/EP2018/075905, filed on Sep. 25, 2018.

(30) Foreign Application Priority Data

Sep. 29, 2017 (DE) .......................... 10 2017 122 820

(51) Int. Cl.
- *A61B 5/02* (2006.01)
- *A61B 5/00* (2006.01)
- *A61B 5/145* (2006.01)
- *A61F 2/06* (2013.01)

(52) U.S. Cl.
CPC ........ *A61B 5/6862* (2013.01); *A61B 5/02007* (2013.01); *A61B 5/14503* (2013.01); *A61F 2/06* (2013.01)

(58) Field of Classification Search
CPC .. A61B 5/00; A61B 5/02; A61B 5/145; A61B 5/6862; A61B 5/14503; A61B 5/02007; A61B 5/14546; A61F 2/06
See application file for complete search history.

(56) References Cited

U.S. PATENT DOCUMENTS

| | | | |
|---|---|---|---|
| 6,280,385 B1 * | 8/2001 | Melzer | G01R 33/286 324/318 |
| 8,016,875 B2 * | 9/2011 | Philipp | A61F 2/86 623/1.42 |
| 8,337,548 B2 | 12/2012 | Klocke et al. | |
| 11,284,840 B1 * | 3/2022 | Xu | A61B 5/6876 |
| 2004/0250819 A1 | 12/2004 | Blair et al. | |
| 2009/0054793 A1 | 2/2009 | Nunez et al. | |

(Continued)

FOREIGN PATENT DOCUMENTS

| | | |
|---|---|---|
| DE | 102007032688 A1 | 1/2009 |
| DE | 102011009695 A1 | 8/2012 |

(Continued)

*Primary Examiner* — Eric J Messersmith
(74) *Attorney, Agent, or Firm* — Laurence A. Greenberg; Werner H. Stemer; Ralph E. Locher

(57) ABSTRACT

An implant (in particular a stent) includes a main structure and a sensor assembly for measuring a body parameter. The sensor assembly includes at least one electrical conductor and at least one capacitor which are connected in such a way that the conductor and the capacitor form at least one electrical resonant circuit. The electrical conductor is surrounded by an electrical insulation. The electrical conductor is in the form of a coil having at least one turn. The capacitor is in contact at least on one side with the surrounding environment and its capacitance changes depending on the body parameter that is to be determined.

10 Claims, 5 Drawing Sheets

(56) References Cited

U.S. PATENT DOCUMENTS

| | | |
|---|---|---|
| 2009/0062900 A1 | 3/2009 | Lal et al. |
| 2011/0115497 A1* | 5/2011 | Cros .................... A61B 5/0031 324/601 |
| 2013/0046166 A1* | 2/2013 | Maleki Jafarabadi ... A61B 3/16 600/398 |
| 2013/0109933 A1* | 5/2013 | Wittchow ............ A61B 5/0031 600/302 |
| 2016/0045316 A1* | 2/2016 | Braido ................. A61B 5/6847 623/2.38 |
| 2019/0076033 A1* | 3/2019 | Sweeney ............. A61B 5/02152 |
| 2019/0246916 A1* | 8/2019 | Kuraguntla .......... A61B 5/0265 |

FOREIGN PATENT DOCUMENTS

| | | |
|---|---|---|
| EP | 1990027 A2 | 11/2008 |
| WO | 2016114468 A1 | 7/2016 |

* cited by examiner

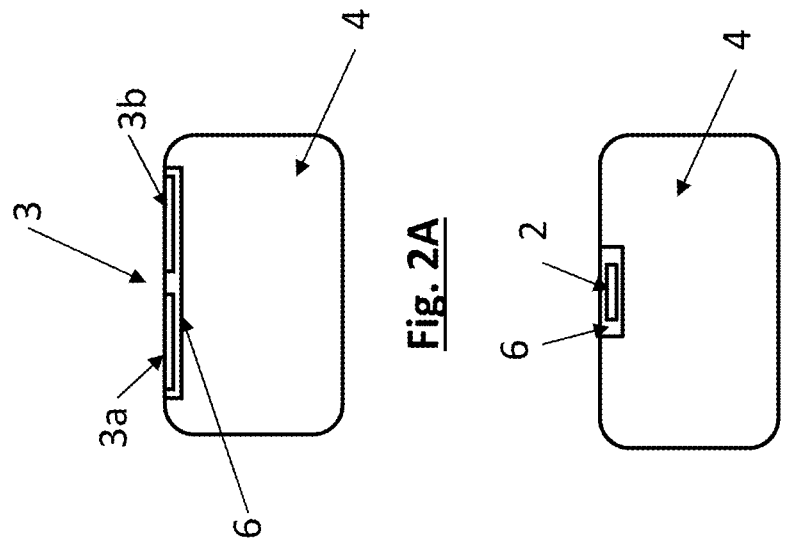
Fig. 2A
Fig. 2B
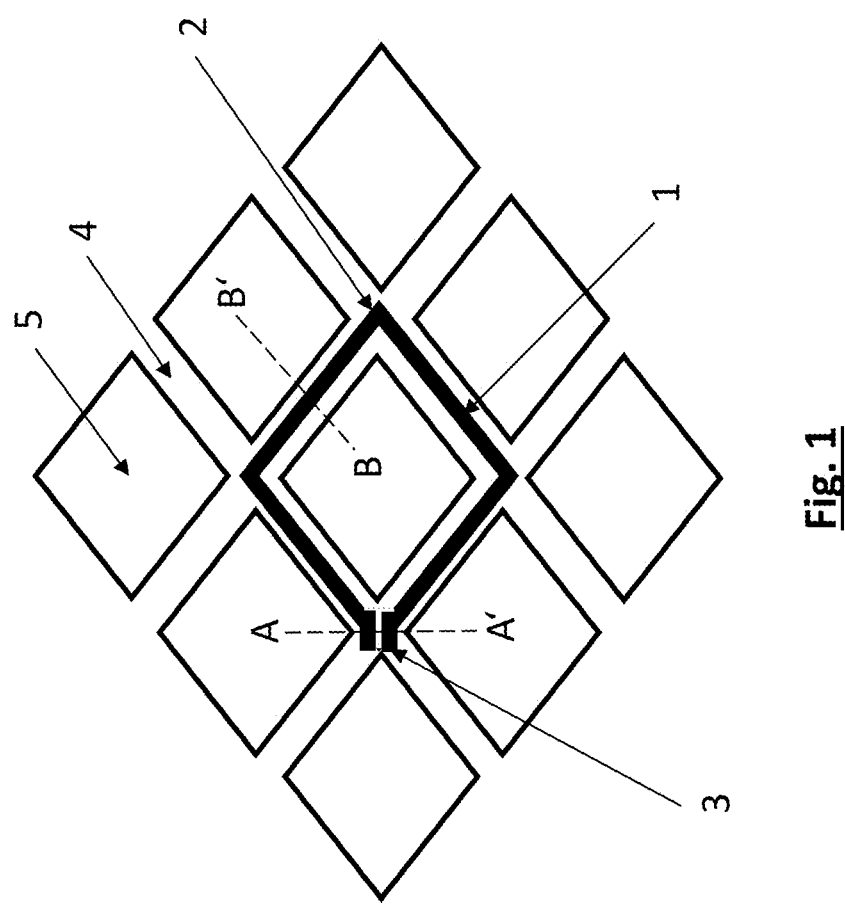
Fig. 1

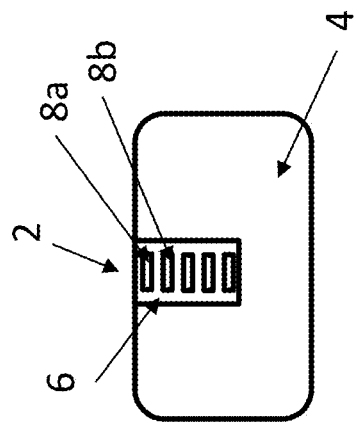
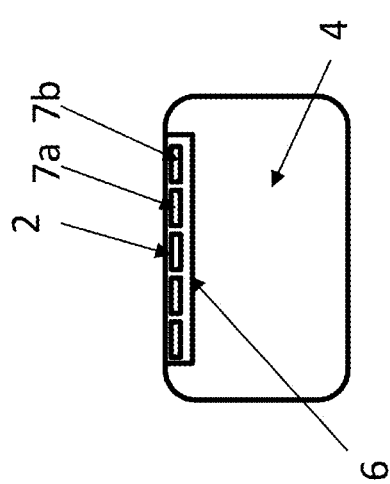
Fig. 4A
Fig. 4B
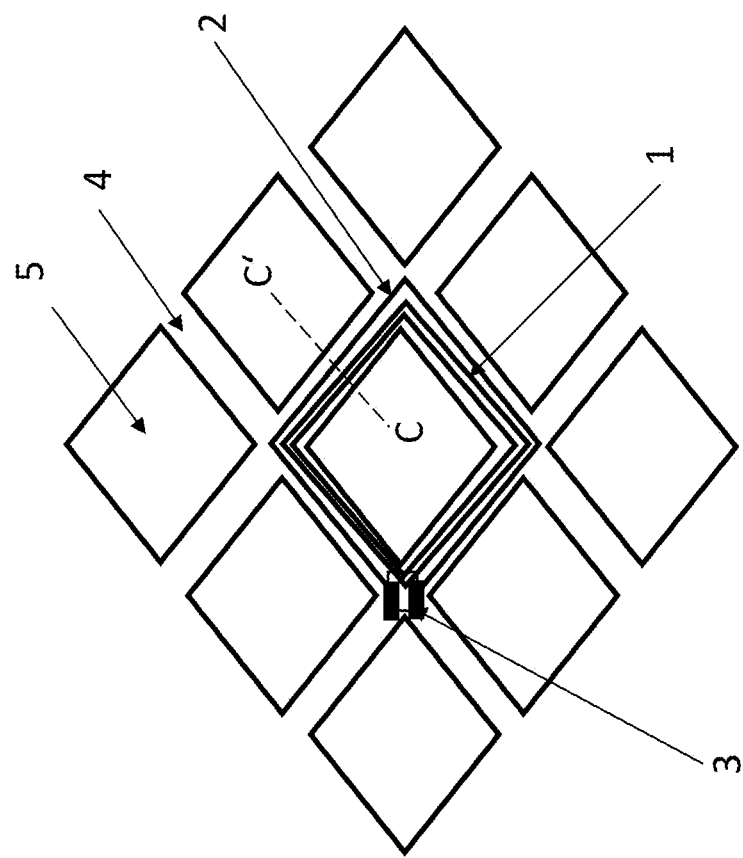
Fig. 3

IMPLANT WITH SENSOR ASSEMBLY

CROSS-REFERENCE TO RELATED APPLICATION

This is a continuation application, under 35 U.S.C. § 120, of copending International Application PCT/EP/2018/075905, filed Sep. 25, 2018, which designated the United States; this application also claims the priority, under 35 U.S.C. § 119, of German Patent Application DE 10 2017 122 820, filed Sep. 29, 2017; the prior applications are herewith incorporated by reference in their entirety.

BACKGROUND OF THE INVENTION

Field of the Invention

The present invention relates to an implant having a main structure and a sensor assembly for measuring a body parameter, wherein the sensor assembly includes at least one electrical conductor and at least one capacitor which are connected in such a way that the conductor and the capacitor form at least one electrical resonant circuit.

The invention will be described hereinafter on the basis of an intraluminal endoprosthesis, in particular on the basis of a stent, wherein the sensor assembly is intended to detect the endothelialisation of the stent. In principle, however, any body parameters from the surroundings of the implant can be detected by using the sensor assembly of the present invention, for example any parameters of the blood (for example cholesterol level, blood sugar, etc.), of the surrounding tissue (for example active substance concentration in the tissue), or parameters of other body structures in contact with the sensor assembly of the implant. Accordingly, a bone implant or another implant from the field of osteopathy, or equally any implant which is implanted temporarily or permanently solely in order to measure a body parameter can be used as an implant.

Various implants including a system of sensors are known from the prior art.

European Patent EP 1 990 027 B1, corresponding to U.S. Pat. No. 8,016,875, discloses a degradable stent, which is formed as a coil and includes a capacitor. The stent itself thus forms a passive resonant circuit which can be excited from outside. The resonance frequency of that resonant circuit changes as a result of the degradation, and therefore the stent itself can be used as a sensor for its degradation.

German Patent Application DE 10 2007 032 688 A1, corresponding to U.S. Pat. No. 8,337,548, discloses a stent which includes a cavity which can be filled with an active substance and a body capable of vibration. The release of the active substance is excited by external excitation of the body capable of vibration.

U.S. Patent Application Publication No. 2009/0062900 discloses a stent including a sensor assembly for determining the endothelialisation of the stent. The sensor actively sends a signal, the characteristic of which changes with increasing endothelialisation.

SUMMARY OF THE INVENTION

It is accordingly an object of the invention to provide an implant with a sensor assembly, which overcomes the hereinafore-mentioned disadvantages of the heretofore-known implants of this general type and which equips the implant in such a way that the implant delivers information regarding at least one body parameter when subject to suitable external excitation.

With the foregoing and other objects in view there is provided, in accordance with the invention, an implant comprising a main structure and a sensor assembly for measuring a body parameter, the sensor assembly including at least one electrical conductor and at least one capacitor which are connected in such a way that the conductor and the capacitor form at least one electrical resonant circuit, the electrical conductor is insulated with respect to the implant and/or another electrical conductor and is disposed in the form of a coil or loop having at least one turn, and the capacitor is in contact with the surrounding environment on at least one side in such a way that its capacitance changes depending on the body parameter that is to be determined.

In accordance with the basic concept of the invention, the implant is provided with at least one passive resonant circuit, which is formed of at least one coil (having at least one turn) and from at least one capacitor. The capacitor is not fully insulated with respect to the surrounding environment and is exposed to changes in the surrounding environment. The surrounding environment of the capacitor accordingly influences the capacitance of the capacitor. If the surrounding environment changes, the capacitance of the capacitor also changes, and therefore so too does the resonance frequency of the resonant circuit. In an ideal case, there is a shift in the resonance frequency (for example when the permittivity of the surrounding environment changes) or a change in the sharpness of the resonance frequency (for example when the conductivity of the surrounding environment changes).

In accordance with the basic concept of the invention, the implant accordingly includes a passive and a non-active sensor assembly. The implant itself therefore does not consume any energy, and the body parameter can be queried as often as desired by an electromagnetic excitation outside the body. In particular, the course over time of the change to the body parameter can thus be tracked.

The resonance frequency of a resonant circuit can be determined as follows:

$$f_{res} \frac{1}{2\pi f} \frac{1}{\sqrt{LC}}$$

The body parameter is detected in accordance with the basic concept of the invention solely by the change to the capacitance of the capacitor. The capacitor at least partially/on one side is not electrically insulated or is not insulated with respect to the surrounding environment. The capacitor is thus in contact with the body at least on one side, in such a way that, in the event of a change to a body parameter in the surrounding environment of the capacitor, the capacitance of the capacitor is also influenced or changes. Accordingly, the change to the body parameter can be determined on the basis of the change in capacitance of the capacitor and the associated change to the resonant circuit.

The electrical conductor(s) is/are advantageously insulated not only with respect to the implant or other electrical conductors, but also with respect to the surrounding environment.

Within the scope of the invention an electrical conductor is understood to mean a material structure which is mounted on the implant or integrated therein and has a higher electrical conductivity than the implant. Materials of this kind are known to a person skilled in the art. The electrical conductors are preferably made of gold, platinum or copper.

Within the scope of the invention a capacitor is understood to mean an assembly formed of at least two planar conductive elements, which are physically separated from one another by a dielectric. Within the scope of the assembly a planar element is understood to mean an element which has a much smaller extent in one spatial direction than in the two other spatial directions, wherein the smaller extent is at most half as great, preferably between ¼ and ¹⁄₁₀₀₀, in particular between ⅕ and ¹⁄₂₀ of the extent in the other two spatial directions. The conductive elements of the capacitor are preferably made of gold, platinum or copper.

The resonant circuits are preferably formed in such a way that their resonance frequency is at most 5 GHz, preferably at most 1 GHz.

The sensor assembly is advantageously mounted on the main structure or integrated in the main structure. The term "integrated in the main structure" within the scope of this application is understood to mean that the main structure of the implant is provided with a cavity or a recess for the sensor assembly. The sensor assembly is integrated in the main structure of the implant in this cavity or in this recess. The term "mounted on the main structure" within the scope of this application is understood to mean a sensor assembly which is suitably fastened on the main structure of the implant. The term "main structure" of the implant is understood within the scope of this application to mean the implant body in its form in the body assumed for fulfilling its purpose. Accordingly, the main body of a stent for example would be the stent structure which in the implanted state provides the supporting function in the vessel.

Both the embodiment of a sensor assembly mounted on the main structure of the implant and the embodiment of a sensor assembly integrated in the main body of the implant have advantages. A sensor assembly mounted on the main structure can be easily produced and does not require any further changes to the actual implant, which frequently is already long-established. If the sensor assembly is integrated in the main structure, by contrast the interaction between implant and body is influenced little, or not at all. If, for example, the implant is a stent, the sensor assembly can be mounted on the luminal side or can be integrated in the stent body on the luminal side. In the first case, the stent can be equipped very easily with a sensor assembly according to the invention, and in the second case the flow of blood is uninfluenced or is only minimally influenced by the sensor assembly.

In the embodiment of a sensor assembly applied to the implant, electrical conductors and capacitors, similarly to a printed circuit board, can be mounted on a suitable substrate, which is then mounted in turn on the implant.

The electrical conductor is preferably disposed in more than one turn, wherein the individual turns are disposed side by side and/or one above the other. Within the scope of this application, the term "side by side" is understood to mean a configuration where the turns of the electrical conductor are disposed side by side based on the plane of the closest outer surface of the implant, i.e. in a plane parallel to the closest outer surface of the implant. The term "one above the other" is understood to mean a configuration of the turns of the electrical conductor one above the other in relation to the plane of the closest outer surface of the implant (i.e. vertical configuration one above the other based on the outer surface of the implant).

In principle, a passive resonant circuit which is formed of a capacitor and a conductor and which is disposed in the form of a coil having one turn is sufficient for the implant according to the invention including the sensor assembly. However, the inductance of the coil can be increased by the use of turns disposed side by side and/or one above the other. The resonance frequency of the resonant circuit can thus be easily adapted in the range below 5 GHz, similarly to the above formula.

In a preferred embodiment the sensor assembly includes at least two resonant circuits disposed in series. This embodiment of the invention is likewise used for adjustment of the resonance frequency of the resonant circuits connected in series to the range beneath 5 GHz. The following is true for the resonance frequency of resonant circuits connected in series:

$$f_{res} = \frac{1}{2\Pi} \frac{1}{\sqrt{(L_1 + L_2 + \ldots L_N)(C_{ges})}}$$

Accordingly, the resonance frequency is lowered in this case by the combination of a plurality of resonant circuits in series, whereby the resonance frequency in the body can be better measured.

In another preferred embodiment the sensor assembly includes at least two resonant circuits, which are electrically and physically separated from one another and each have different inherent frequencies. The term "inherent frequency" within the scope of this application is understood to mean the resonance frequency of the resonant circuit formed of coil and capacitor that the present circuit has without the influence of the body parameter on the capacitance of the capacitor. This embodiment of the invention accordingly allows a spatial resolution of the influence of the body parameter on the individual capacitances of the capacitors of the various resonant circuits.

At least two resonant circuits particularly preferably differ with respect to the spatial orientation of the coils of the resonant circuits. A different spatial orientation of the coils is understood within the scope of this application to mean an angle between 0° and 180° between the surface normals of the area included by the coil (the turns of the coil). In the case of a coil formed of one turn, the surface normal is accordingly perpendicular to the plane of the surface in which the turn lies. In the case of a cylinder coil the surface normal corresponds to the cylinder axis of the cylinder coil.

The detection of the body parameter is based on a change to the capacitance of the capacitor and therefore to a change to the resonance frequency of the passive resonant circuit formed of conductor and the capacitor. The resonance frequency of the resonant circuit is determined through an external electromagnetic excitation. The conductor disposed in the form of a coil must also encompass an electromagnetic alternating field for the excitation and corresponding detection of the resonance frequency of the resonant circuit of the sensor assembly. Accordingly, only the electromagnetic field encompassed by the coil contributes to the measurement. In order to ensure that at least one coil of a resonant circuit encompasses an electromagnetic field, at least two, preferably more than two, in particular 4 to 20, resonant circuits are disposed in this embodiment of the invention in such a way that the coils of the resonant circuits each have a different spatial orientation.

This embodiment of the invention can be combined with both of the previously described embodiments. If a plurality of resonant circuits with different spatial orientation of the coils are connected in series, it can be ensured that at least one coil encompasses the exciting external electrical field. In the case of physically and electrically separated resonant circuits of different spatial orientation, an improved physical allocation of the measured body parameter can thus likewise be achieved. The connection of resonant circuits of different inherent frequency in series is also possible.

The implant is preferably formed as an intraluminal endoprosthesis, in particular as a stent, and the endothelialization of the stent, blood parameters and/or active substance concentrations in the blood and/or tissue is measured as body parameter.

This embodiment of the invention is particularly preferred and suitable for research. The sensor assembly according to the invention offers a simple possibility for determining the endothelialization of a stent over time. The sensor assembly can be mounted on the main structure (the main frame) of the stent or particularly preferably can be integrated in the main structure of the stent. In this case, indentations are cut into the stent struts by using laser (for example using a material-removing femtosecond laser), into which the electrical conductors are fitted with their insulation and the partially insulated capacitor. The capacitor is not insulated on the luminal side of the stent and is thus in contact with the blood directly after implantation. Following the implantation, the endothelialization of the stent begins, i.e. the stent grows into the wall of the blood vessel. Accordingly, the luminal side of the stent is also coated with endothelial cells of the vessel wall, and the capacitor is no longer in contact with the blood. The resultant change in capacitance of the capacitor leads to a change in the resonance frequency of the resonant circuit, whereby the endothelialization of the stent can be detected.

At least two resonant circuits are further preferably distributed over the periphery of the implant and disposed in series. The periphery of an intraluminal implant is understood to mean the periphery of the lumen formed by the intraluminal endoprosthesis. In this embodiment of the invention at least two, preferably 4 to 20, resonant circuits are distributed over the periphery of the implant. In this embodiment of the invention it is ensured that at least one coil encompasses the exciting external electrical field, and the adjustment of the resonance frequency below 1 GHz is facilitated by the series connection of the resonant circuits.

In a further, also combinable embodiment, the implant includes at least two resonant circuits, which are electrically and physically separated from one another, wherein a physical separation exists with respect to the longitudinal axis of the implant. Within the scope of the application the longitudinal axis of the implant is understood to mean the axis of the lumen surrounded by the implant. In this embodiment of the invention the physical course of endothelialization (for example in relation to the blood flow) can be determined.

Other features which are considered as characteristic for the invention are set forth in the appended claims.

Although the invention is illustrated and described herein as embodied in an implant with a sensor assembly, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 is a diagrammatic, perspective view of a stent with the simplest form of a sensor assembly according to the invention;

FIG. 2A is a sectional view through a stent strut along the line of section AA' from FIG. 1;

FIG. 2B is a sectional view through a stent strut along the line of section BB' from FIG. 1;

FIG. 3 is a perspective view of a stent with a sensor assembly with a coil having a number of turns;

FIG. 4A is a sectional view through a possible configuration of the conductor along the line of section CC' through a stent strut from FIG. 3;

FIG. 4B is a sectional view through an alternative configuration of the conductor along the line of section CC' through a stent strut from FIG. 3;

DETAILED DESCRIPTION OF THE INVENTION

Figure 5:
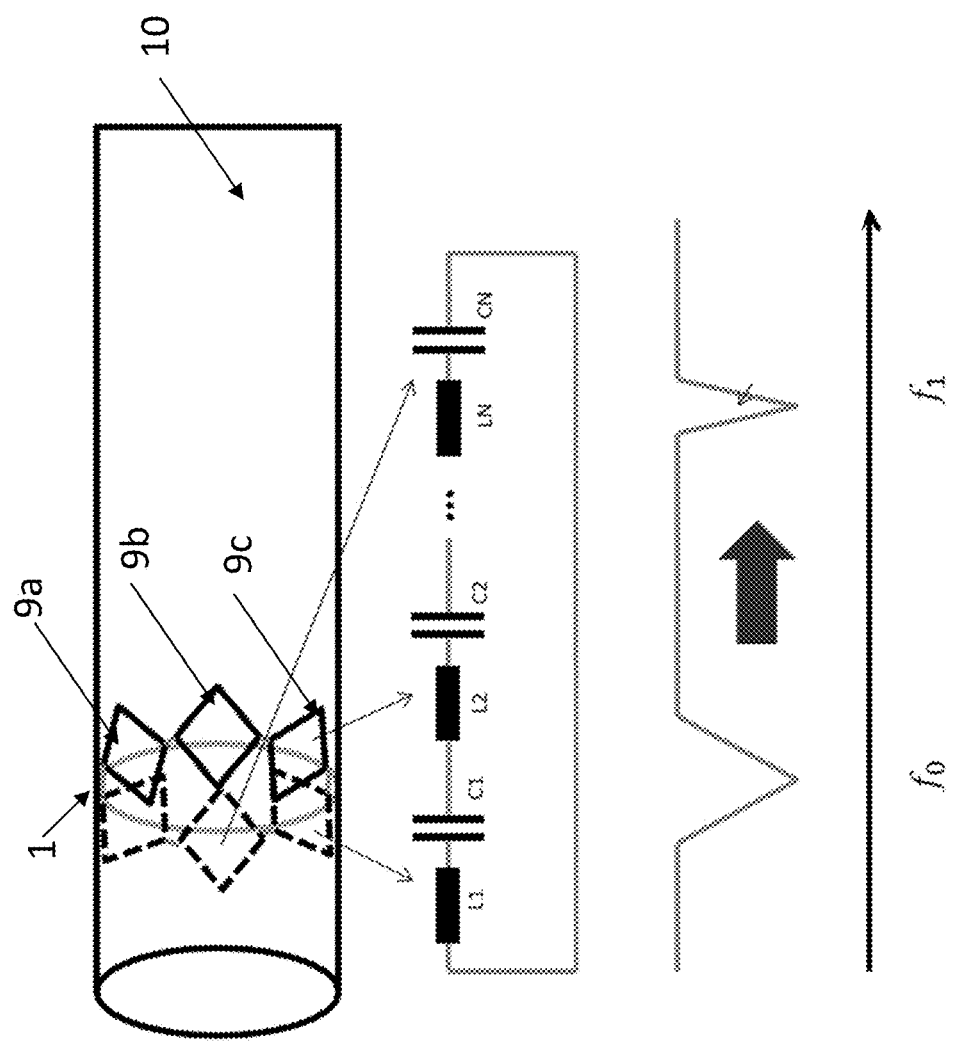
FIG. 5 is a perspective view of a stent with resonant circuits disposed in series over the periphery.

Referring now to the figures of the drawings in detail and first, particularly, to FIG. 1 thereof, there is seen a detail of a planar development of a stent with stent struts 4 forming a main structure and free spaces 5 formed between the struts. A cell includes the simplest embodiment of a sensor assembly according to the invention, which is formed of a conductor 2 and a capacitor 3.

Both the conductor 2 and the capacitor 3 are integrated in the main structure of the stent, as is shown by the sections along lines AA' (FIG. 2A) and BB' (FIG. 2B). The stent strut 4 is provided with a recess filled by the conductor 2 and associated insulation 6 (FIG. 2B). As shown by the section along line BB' in FIG. 2A, the capacitor 3 is also integrated in a recess in the stent strut 4. In this case, however, the electrical insulation 6 is disposed only on the sides towards the stent strut 4. Upwardly in FIG. 2A (luminally in the case of implantation), the capacitor 3 is not electrically insulated. In this case, directly after implantation, the blood forms the dielectric of the capacitor 3. If the stent is endothelialized, the luminal side (at the top in FIG. 2A) is also covered by endothelial cells, which then form the dielectric of the capacitor 3. In the event of external electromagnetic excitation, the endothelialization can be detected through the resultant change to the capacitance and resonance frequency of the resonant circuit formed of the conductor 2 and capacitor 3. In order to further increase the area for the dielectric and make the configuration more sensitive, a space (the gap) between the two planar elements 3a, 3b (see FIG. 7) of the capacitor 3 can also be left free. In this embodiment electrical insulation would be applied only to the surfaces of the capacitor 3 adjacent the stent.

FIGS. 3, 4A and 4B show a similar sensor assembly, wherein however, in contrast to FIG. 1, the conductor 2 is disposed in the form of a number of turns forming a coil. In this case, FIG. 4A shows the section along CC' through the stent strut 4 and a number of conductors 2 which are disposed side by side in turns 7a, 7b. FIG. 4B shows an alternative configuration of the conductor 2 in turns 8a, 8b. In this case, the turns 8a, 8b are disposed one above the other.

FIG. 5 diagrammatically shows a stent 10 including a sensor assembly 1 formed of a number of resonant circuits 9a, 9b and 9c, which are disposed along the periphery and are connected in series. FIG. 5 also shows the associated equivalent circuit diagram having inductors L1, L2 ... LN and capacitors C1, C2 ... CN and the change to the resonance frequency from $f_0$ to $f_1$ in the event of endothelialization of the stent.

Figure 6:
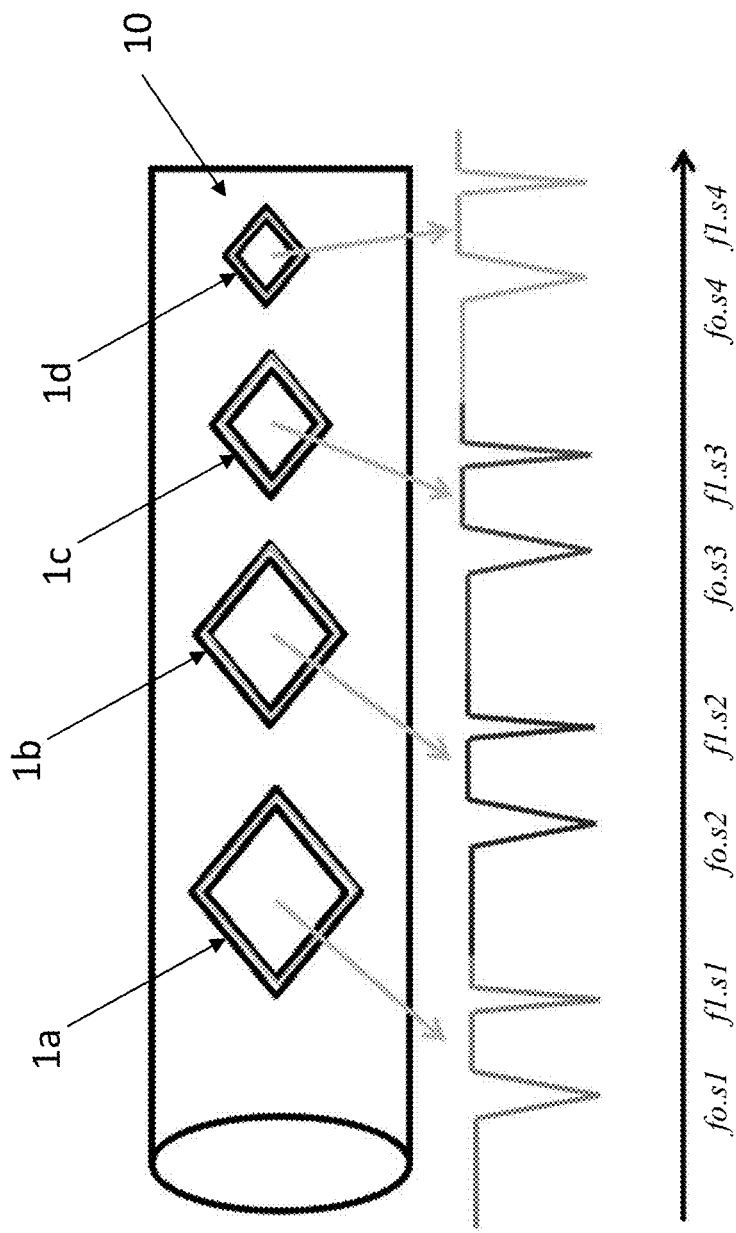
FIG. 6 is a perspective view of a stent with a plurality of physically and electrically separate resonant circuits.

FIG. 6 diagrammatically shows a stent 10 with a sensor assembly, in which a plurality of resonant circuits 1a, 1b, 1c, 1d separated from one another physically and electrically and having different inherent frequencies f are disposed along the longitudinal axis of the stent.

Figure 7:
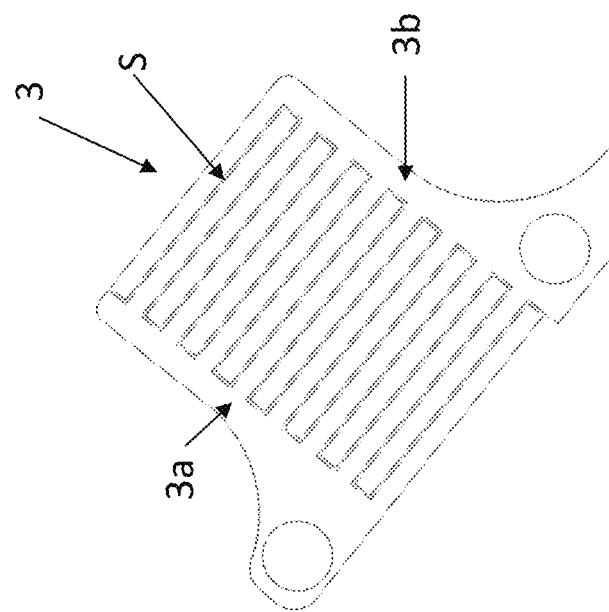
FIG. 7 is a fragmentary, plan view of an alternative embodiment of a capacitor.

FIG. 7 shows an alternative embodiment of a capacitor 3. In this embodiment of the capacitor 3, the two planar elements 3a and 3b engage with one another in a finger-shaped manner. In this embodiment the planar elements 3a and 3b are insulated merely with respect to the stent. A gap S between the two planar elements 3a and 3b is not filled with a material in addition to the electrical insulation. In this case, the surrounding medium forms the dielectric. Due to the finger-shaped engagement with one another of the two elements 3a and 3b, the gap S is very long and therefore the area for the dielectric, which is exposed to the changes in the surrounding environment, is maximized.

The invention claimed is:

1. An implant, comprising:
a main structure formed by a plurality of struts and free spaces formed between said plurality of struts;
a sensor assembly for measuring a body parameter, said sensor assembly including at least one electrical conductor and at least one capacitor;
said at least one electrical conductor and said at least one capacitor being connected to form at least one electrical resonant circuit;
said at least one electrical conductor being a coil having at least one turn;
said coil disposed in a cavity or recess of one or more of said plurality of struts, and said at least one capacitor being mounted directly on, or integrated into, one or more of said plurality of struts;
said at least one capacitor being in contact at least on one side with a surrounding environment and having a capacitance changing in dependence on the body parameter to be determined; and
said electrical conductor being insulated with respect to at least one of the implant or another electrical conductor.

2. The implant according to claim 1, wherein said at least one electrical conductor has a plurality of individual turns, and said individual turns are disposed at least one of side by side or one above another.

3. The implant according to claim 1, wherein said sensor assembly includes at least two resonant circuits being electrically and physically separated from one another, said at least two resonant circuits having different inherent frequencies.

4. An implant, comprising:
a main structure formed by a plurality of struts and at least one free space formed between said plurality of struts;
a sensor assembly for measuring a body parameter, said sensor assembly including at least one electrical conductor and at least one capacitor;
said at least one electrical conductor and said at least one capacitor being connected to form at least one electrical resonant circuit;
said at least one electrical conductor being a coil having at least one turn;
said capacitor being mounted directly on, or integrated into, at least one of said plurality of struts, with said coil being disposed in a cavity or recess of said plurality of struts surrounding said at least one free space formed between said plurality of struts;
said at least one capacitor being in contact at least on one side with a surrounding environment and having a capacitance changing in dependence on the body parameter to be determined; and
said electrical conductor being insulated with respect to at least one of the implant or another electrical conductor.

5. An implant, comprising:
a main structure formed by a plurality of struts and free spaces formed between said plurality of struts;
a sensor assembly for measuring a body parameter, said sensor assembly including at least one electrical conductor and at least one capacitor;
said at least one electrical conductor and said at least one capacitor being connected to form at least one electrical resonant circuit;
said at least one electrical conductor being a coil having at least one turn;
said coil and said at least one capacitor being mounted directly on, or integrated into, one or more of said plurality of struts;
said at least one capacitor being in contact at least on one side with a surrounding environment and having a capacitance changing in dependence on the body parameter to be determined;
said electrical conductor being insulated with respect to at least one of the implant or another electrical conductor; and
wherein said sensor assembly includes at least two resonant circuits disposed in series.

6. The implant according to claim 5, wherein said at least two resonant circuits differ with respect to a spatial orientation of said coils of said resonant circuits.

7. The implant according to claim 5, wherein the implant is formed as an intraluminal endoprosthesis experiencing endothelialization, and at least one of the endothelialization, blood parameters or active substance concentrations in at least one of the blood or tissue are measured as the body parameter.

8. The implant according to claim 7, wherein the intraluminal endoprosthesis is as a stent.

9. The implant according to claim 7, wherein said at least two resonant circuits are distributed over a periphery of the implant and are disposed in series.

10. The implant according to claim 7, wherein said at least two resonant circuits are electrically and physically separated from one another with respect to a longitudinal axis of the implant.

* * * * *